United States Patent
Tsuji et al.

(10) Patent No.: US 7,271,281 B2
(45) Date of Patent: Sep. 18, 2007

(54) PREPARATION OF 2,3,3',4'-BIPHENYL-TETRACARBOXYLIC ACID TETRAESTER

(75) Inventors: Tetsuro Tsuji, Yamaguchi (JP); Yasushi Yamamoto, Yamaguchi (JP); Shinji Yasuda, Yamaguchi (JP)

(73) Assignee: Ube Industries, Ltd., Yamaguchi (JP)

( * ) Notice: Subject to any disclaimer, the term of this patent is extended or adjusted under 35 U.S.C. 154(b) by 344 days.

(21) Appl. No.: 10/971,132

(22) Filed: Oct. 25, 2004

(65) Prior Publication Data

US 2005/0090683 A1  Apr. 28, 2005

(30) Foreign Application Priority Data

Oct. 23, 2003 (JP) ............................. 2003-363188

(51) Int. Cl.
*C07C 69/76* (2006.01)
*C07C 67/00* (2006.01)

(52) U.S. Cl. .......................... 560/76; 560/96
(58) Field of Classification Search ................. 560/76, 560/96

See application file for complete search history.

(56) References Cited

U.S. PATENT DOCUMENTS 4,008,266 A * 2/1977 Intille .......................... 560/96
4,581,469 A * 4/1986 Itatani et al. .................. 560/96

* cited by examiner

*Primary Examiner*—Taylor Victor Oh
(74) *Attorney, Agent, or Firm*—Nixon Peabody LLP; Jeffrey L. Costellia

(57) ABSTRACT

2,3,3',4'-Biphenyltetracarboxylic acid tetraester is predominantly produced by a process in which a phthalic acid diester is subjected to oxidative-coupling reaction in the presence of molecular oxygen and a catalyst comprising a rhodium-containing compound.

8 Claims, No Drawings

PREPARATION OF 2,3,3',4'-BIPHENYL-TETRACARBOXYLIC ACID TETRAESTER

FIELD OF THE INVENTION

The present invention relates to a process for preparing 2,3,3',4'-biphenyltetracarboxylic acid tetraester.

BACKGROUND OF THE INVENTION

A biphenyltetracarboxylic acid tetraester can be converted to a biphenyltetracarboxylic acid dianhydride which is favorably employed to prepare heat-resistant aromatic polyimide. The biphenyltetracarboxylic acid tetraester can be generally classified into 3,3',4,4'-biphenyltetracarboxylic acid tetraester (i.e., s-BPTT) and 2,3,3',4'-biphenyltetracarboxylic acid tetraester (i.e., a-BPTT). The s-BPTT is favorably employable for preparing highly heat-resistant polyimide, while the a-BPTT is favorably employable for preparing thermoplastic polyimide.

Japanese Patent Provisional Publication 55-141417 describes a process for preparing a biphenyltetracarboxylic acid tetraester from phthalic diester in the presence of molecular oxygen and a catalyst comprising an organic palladium compound and a copper compound. The resulting biphenyltetracarboxylic acid tetraester mainly comprises s-BPTT (3,3',4,4'-biphenyltetracarboxylic acid tetraester).

Japanese Patent Provisional Publication 61-106541 describes a process for preparing a biphenyltetracarboxylic acid tetraester mainly comprising a-BPTT (i.e., 2,3,3',4'-biphenyltetracarboxylic acid tetraester) from phthalic diester in the presence of molecular oxygen and a catalyst comprising an organic palladium compound and a copper compound and under such condition that a β-diketone is continuously or intermittently supplied into the reaction mixture.

Japanese Patent Provisional Publication 2003-113143 describes a process for preparing a biphenyltetracarboxylic acid tetraester mainly comprising a-BPTT from phthalic diester in the presence of molecular oxygen and a catalyst comprising a palladium complex compound having a ligand molecule containing nitrogen and oxygen.

Japanese Patent Provisional Publication 2000-302700 describes an oxidative-coupling reaction between olefin and an aromatic compound in the presence of rhodium acetylacetonato catalyst and a copper(II) redox reagent.

SUMMARY OF THE INVENTION

The present invention has an object to provide a new process for preparing a-BPTT (i.e., 2,3,3',4'-biphenyltetracarboxylic acid tetraester) from phthalic diester.

The present invention resides in a process for preparing 2,3,3',4'-biphenyltetracarboxylic acid tetraester which comprises subjecting a phthalic acid diester to oxidative-coupling reaction in the presence of molecular oxygen and a catalyst comprising a rhodium-containing compound.

Preferred embodiments of the invention are as follows:

(1) The catalyst further comprises a copper-containing compound such as copper acetate or [1,3-bis(2,6-diisopropylphenyl)imidazolium]copper(I) chloride.

(2) The rhodium-containing compound is a rhodium acetylacetonato complex.

(3) The rhodium-containing compound is a rhodium 1,5-cyclooctadiene complex.

(4) The rhodium-containing compound is represented by the following formula:

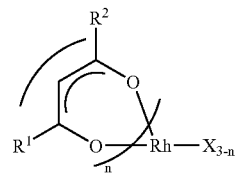

in which each of $R^1$ and $R^2$ independently represents an alkyl group or an aryl group, X represents a halogen atom, and n is an integer of 1 to 3.

(5) The catalyst further comprises β-diketone.

DETAILED DESCRIPTION OF THE INVENTION

The phthalic acid diester employable in the invention can be a phthalic acid dialkylester or a phthalic acid diarylester. The alkyl group preferably has 1 to 8 carbon atoms. Examples of the phthalic acid dialkylesters include dimethyl phthalate, diethyl phthalate, dipropyl phthalate, dibutyl phthalate, and dioctyl phthalate. An example of the phthalic acid diarylester is diphenyl phthalate.

The catalyst employed in the process of the invention comprises a rhodium-containing compound. It is preferred that the catalyst further comprises each or both of β-diketone and a copper-containing compound.

Examples of the rhodium-containing compounds include rhodium halides such as rhodium chloride, rhodium bromide, rhodium iodide, dirhodium di-μ-chlorotetra(carbonyl), di-μ-chlorotetra(ethylene)dirhodium, di-μ-chlorotetra(cyclooctene)dirhodium, and di-μ-chlorobis(1,5-cyclooctadiene)dirhodium, carbonylrhodiums such as dodecacarbonyltetrarhodium, hexadecacarbonylhexarhodium, tetracarbonylrhodium hydride, and acetylacetonatobis-(carbonyl)rhodium, rhodium carboxylates such as rhodium acetate and rhodium trifluoroacetate, and acetylaceto-nato-bis(ethylene)rhodium. The rhodium-containing compound can be anhydride or a hydrated compound.

The following rhodium-containing compound or its hydrate is particularly preferred because this compound shows a high catalytic activity:

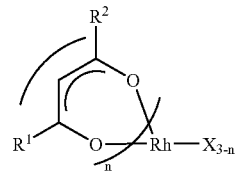

in which each of $R^1$ and $R^2$ independently represents an alkyl group or an aryl group (the alkyl or aryl group may contain one or more substituents), x represents a halogen atom such as F, Cl, Br or I, and n is an integer of 1 to 3.

Examples of the rhodium-containing compounds represented by the above-identified formula include tris-(acetylacetonato)rhodium, chlorobis(acetylacetonate)-rhodium, tris(1,1,1,5,5,5-hexafluoro-acetylacetonate)-rhodium, tris(1,3-diphenyl-1,3-propanedionate)rhodium, and chlorobis (acetylacetonate)rhodium. These compounds can be employed in the form of anhydride or hydrated compound.

The rhodium-containing compound of the formula can be prepared by reacting rhodium halide and an enolate compound obtained from a corresponding dicarbonyl compound and a base (described in Japanese Patent Provisional Publication 2000-302700) or by reacting rhodium hydroxide obtained from rhodium nitrate and acetylacetone (described in J. Am. Chem. Soc., 1953, 75, 984-985).

The rhodium-containing compound can be previously prepared in advance of placing in the reaction mixture. Otherwise, the rhodium-containing compound can be produced in the reaction mixture by placing appropriate starting compounds of the rhodium-containing compound in the reaction mixture. For instance, a rhodium salt and a ligand compound can be simultaneously or separately placed in the reaction mixture so as to in situ produce the rhodium-containing compound of the formula.

The reaction of the process according to the invention can be carried out by employing the rhodium-containing compound in an amount of 0.00001 to 0.05 mol (preferably not less than 0.00005 mol and not more than 0.01 mol) per one mol of the phthalic diester.

The reaction can be accelerated by employing a copper-containing compound in combination with the rhodium-containing compound. Examples of the copper-containing compound include copper acetate, copper propionate, copper n-butylate, copper 2-methylpropionate, copper pivalate, copper lactate, copper isobutylate, copper benzoate, copper trifluoroacetate, bis(acetylacetonate)copper, bis(1,1,1,5,5,5-hexafluoroacetylacetonate)copper, copper chloride, copper bromide, copper iodide, copper nitrate, copper nitrite, copper sulfate, copper phosphate, copper oxide, copper hydroxide, copper trifluoromethanesulfonate, copper p-toluenesulfonate, and copper cyanide. The copper compound can be employed in the form of anhydride or a hydrated compound. Specifically preferred are copper acetate, copper propionate, copper n-butylate, bis-(acetylacetonato)copper and copper pivalate.

Also employable are copper-containing compounds in which a hetero atom-containing carbene compound is attached to a copper atom. Examples include [1,3-bis(2,6-diisopropylphenyl)imidazolium]copper(I) chloride, [1,3-bis(2,4,6-trimethylphenyl)imidazolium]copper(I) chloride, and [1,3-di-1-adamantyl-imidazolium]copper(I) chloride.

The copper-containing compounds in which a hetero atom-containing carbene compound is attached to a copper atom can be previously prepared in advance of placing in the reaction mixture. Otherwise, the hetero atom-containing carbene compound and a copper compound can be added simultaneously or separately to the reaction mixture, so as to in situ produce the desired copper-containing compound.

The copper-containing compound can be preferably employed in 0.01 to 100 equivalents, more preferably 0.1 to 100 equivalents, per one equivalent of the rhodium-containing compound.

The rhodium-containing compound is advantageously employed in combination with β-diketone. The addition of β-diketone to the reaction mixture containing the rhodium-containing compound is effective to prevent deactivation of the catalytic activity of the rhodium-containing compound.

The β-diketone can be represented by the following formula:

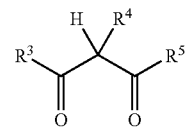

in which each of $R^3$ and $R^5$ independently represents an alkyl group (particularly, alkyl having 1-5 carbon atoms) or an aryl group, each of the groups possibly having one or more substituents.

Examples of β-diketones include acetylacetone, 1,1,1,5,5,5-hexafluoro-acetylacetone, and 1,3-diphenyl-1,3-propanedione.

The β-diketone can be employed in an amount of 0.01 to 50 equivalents, particularly 0.01 to 10 equivalents, per one equivalent of the rhodium-containing compound.

The reaction can be performed in the presence or absence of a solvent. Examples of the solvents include carboxylic acid esters such as ethyleneglycol diacetate and dimethyl adipate, and ketones such as n-butyl methyl ketone, methyl ethyl ketone and isopropyl ethyl ketone. The solvent can be used in 1 to 10,000 equivalents, preferably 1 to 1,000 equivalents, per one equivalent of the phthalic acid diester.

The reaction can be carried out at a temperature of 50 to 300° C., preferably 150 to 260° C., more preferably 180 to 250° C.

The reaction is carried out in an atmospheric condition in which molecular oxygen is present. The molecular oxygen can be non-diluted oxygen gas or oxygen gas diluted with inert gas such as nitrogen gas or carbon dioxide gas to give a gaseous mixture containing approx. 5 to 50 vol. % of oxygen.

There is no specific limitation with respect to reaction pressure, but the reaction is generally carried out at a pressure of 0.2 to 5 atms. in term of an oxygen pressure, or surrounding pressure to 25 atms. in term of airy pressure. The reaction can be carried out in a closed system containing the molecular oxygen or in a vessel to which the molecular oxygen is continuously supplied.

The catalyst composition can be added simultaneously to the reaction system or can be divided and intermittently added to the reaction system.

The reaction can be carried out in an optionally selected reaction vessel by a batch system, a continuous system, or a combination of a batch system and a continuous system.

According to the reaction of the process of the invention, the desired a-BPTT (2,3,3',4'-biphenyltetracarboxylic acid tetraester can be produced at a selectivity of 60 to 99 mol. %, specifically 70 to 99 mol. %. Most of remaining reaction products comprises 3,3',4,4'-bi-phenyltetracarboxylic acid tetraester (s-BPTT).

Thus produced a-BPTT can be isolated or purified by the known procedures such as distillation or crystallization. The isolated or purified a-BPTT can be hydrolyzed at a combination of a high temperature and a high pressure or by the contact with an acid or an alkali, to give 2,3,3',4'-biphenyltetracarboxylic acid, which can be converted into its dianhydride by heating it at a high temperature.

The present invention is further described by the following working examples.

In the following examples, the yield, TON (Turnover Number), and S/A (ratio of reaction products, s-BPTT/a-BPTT) were calculated by the following formulas:

Yield (%)=2×[(total molar amount of produced s-BPTT and a-BPTT)/(molar amount of employed dimethyl phthalate)]×100

TON=(total molar amount of produced s-BPTT and a-BPTT)/(molar amount of rhodium atom in the employed catalyst)

S/A=(molar amount of produced s-BPTT)/(molar amount of produced a-BPTT)

In the following examples, tris(acetylacetonato)-rhodium was prepared by reacting rhodium hydroxide (converted from rhodium nitrate) and acetylacetone. Other rhodium complexes were prepared by reacting a trivalent rhodium halide with an enolate compound (prepared from a corresponding dicarbonyl compound and a base).

[1,3-Bis(2,6-diisopropylphenyl)imidazolium]copper(I) chloride employed in Examples 8 and 9 was prepared by the following procedures.

In a 25 mL-volume Schlenk's tube were placed 298 mg (0.70 mmol) of 1,3-bis(2,6-diisopropylphenyl)imidazolium chloride, 67.6 mg (0.70 mmol) of sodium t-butoxide, and 73.4 mg (0.74 mmol) of copper(I) chloride. The inner atmosphere was purged with Ar gas three times. To the content of the tube was added 5 mL of anhydrous tetrahydrofuran (solvent) by means of a micro-syringe. The resulting mixture was stirred for 4 hours at room temperature. After the reaction was complete, the reaction mixture was filtered by celite to remove insolubles. The resulting solution was then concentrated. The concentrated product was brought into contact with a mixture of methylene chloride and diethyl ether, to precipitate 246 mg (0.50 mmol., yield 71%) of [1,3-Bis(2,6-diisopropylphenyl)imidazolium]copper(I) chloride as a white solid product.

$^1$H-NMR (CD$_2$Cl$_2$, 300 MHz): 1.23 (d, 12H), 1.28 (d, 12H), 2.52-2.62 (m, 4H), 7.18 (s, 2H), 7.34 (d, 4H), 7.53 (dd, 2H)

Elementary analysis: Found(%): C 66.44, H 7.28, N 5.77, Calculated(%) for C$_{27}$H$_{36}$ClCuN$_2$: C 66.51, H 7.44, N 5.75

EXAMPLE 1

In a 20 mL-volume pear type glass flask were placed 1.27 g (6.5 mmol) of dimethyl phthalate and 20.3 mg (0.051 mmol) of tris(acetylacetonato)rhodium. To the flask were attached a Liebig condenser and a balloon containing air (approx. 1 atm.). The flask was then placed in a silicone oil bath previously heated to 200° C. The content in the flask was stirred for 6 hours while cooling water was passed through the Liebig condenser. After the reaction was complete, the flask was cooled in air, and the reaction mixture was diluted with acetone. The diluted reaction mixture was subjected to gas chromatography after addition of cholesterol acetate (internal standard). The following analytical results were obtained:

Yield: 2.8%, TON: 1.8, S/A: 2/98

EXAMPLE 2

The procedures of Example 1 were repeated except that 1.27 g (6.5 mmol) of dimethyl phthalate, 20.2 mg (0.050 mmol) of tris(acetylacetonato)rhodium, and 3.2 mg (0.016 mmol) of copper acetate monohydrate were placed in the flask.

The following analytical results were obtained:

Yield: 5.2%, TON: 3.4, S/A: 3/97

EXAMPLE 3

The procedures of Example 1 were repeated except that 1.27 g (6.5 mmol) of dimethyl phthalate and 18.0 mg (0.051 mmol) of chlorobis(acetylacetonato)rhodium monohydrate were placed in the flask.

The following analytical results were obtained:

Yield: 2.9%, TON: 1.9, S/A: 2/98

EXAMPLE 4

The procedures of Example 1 were repeated except that 1.27 g (6.5 mmol) of dimethyl phthalate, 17.6 mg (0.050 mmol) of chlorobis(acetylacetonato)rhodium monohydrate, and 3.2 mg (0.016 mmol) of copper acetate monohydrate were placed in the flask.

The following analytical results were obtained:

Yield: 5.3%, TON: 3.4, S/A: 3/97

EXAMPLE 5

The procedures of Example 1 were repeated except that 1.27 g (6.5 mmol) of dimethyl phthalate, 12.2 mg (0.026 mmol) of di-μ-chlorobis(1,5-cyclooctadiene)di-rhodium, 2.9 mg (0.015 mmol) of copper acetate monohydrate, and 4.9 mg (0.049 mmol) of acetylacetone were placed in the flask.

The following analytical results were obtained:

Yield: 3.3%, TON: 2.2, S/A: 3/97

EXAMPLE 6

The procedures of Example 1 were repeated except that 1.26 g (6.5 mmol) of dimethyl phthalate, 12.4 mg (0.025 mmol) of di-μ-chlorobis(1,5-cyclooctadiene)di-rhodium, 2.9 mg (0.015 mmol) of copper acetate monohydrate, and 9.8 mg (0.097 mmol) of acetylacetone were placed in the flask.

The following analytical results were obtained:

Yield: 4.0%, TON: 2.6, S/A: 2/98

EXAMPLE 7

In a 300 mL-volume separable flask were placed 239 g (1.23 mol) of dimethyl phthalate and 40.5 mg (0.203 mmol) of copper(II) acetate monohydrate. To the flask were attached a thermometer, a Dimroth condenser, a mechanical stirrer, and a ball filter. The flask was placed in a heated silicone oil bath and the content was stirred, while air was introduced at a rate of 130 mL/min. through the ball filter, and a cooling water was passed through the condenser. At 80° C. (temperature of the reaction mixture), a yellow liquid mixture of 1.789 g (9.17 mmol) of dimethyl phthalate and 53.4 mg (0.133 mmol) of tris-(acetylacetonato)rhodium was added to the reaction mixture, and the reaction mixture was further heated to reach 240° C. and stirred for 2 hours at the temperature. Then, the same liquid mixture was further added to the reaction mixture, and the reaction mixture was further stirred for 2 hours. Then, the same liquid mixture was again added and further stirred for 4 hours. After the reaction was complete, the flask was cooled in air, and the reaction mixture was diluted with methanol and water. The diluted reaction mixture was subjected to liquid chromatography. The following analytical results were obtained:

Yield: 4.5%, TON: 71, S/A: 18/82

EXAMPLE 8

In a 300 mL-volume separable flask were placed 238 g (1.23 mol) of dimethyl phthalate and 97.5 Mg (0.200 mmol) of [1,3-bis(2,6-diisopropylphenyl)imidazolium]copper(I) chloride. To the flask were attached a thermometer, a Dimroth condenser, a mechanical stirrer, and a ball filter. The flask was placed in a heated silicone oil bath and the content was stirred, while air was introduced at a rate of 130 mL/min. through the ball filter, and a cooling water was passed through the condenser. At 80° C. (temperature of the reaction mixture), a yellow liquid mixture of 1.78 g (9.17 mmol) of dimethyl phthalate and 53.4 mg (0.133 mmol) of tris(acetylacetonato)rhodium was added to the reaction mixture, and the reaction mixture was further heated to reach 220° C., and stirred for 2 hours at the temperature. Then, the same liquid mixture was further added to the reaction mixture, and the reaction mixture was further stirred for 2 hours. Then, the same liquid mixture was again added and further stirred for 4 hours. After the reaction was complete, the flask was cooled in air, and the reaction mixture was diluted with methanol and water. The diluted reaction mixture was subjected to liquid chromatography. The following analytical results were obtained:

Yield: 1.3%, TON: 20, S/A: 22/78

EXAMPLE 9

In a 300 mL-volume separable flask were placed 238 g (1.23 mol) of dimethyl phthalate and 98.0 mg (0.201 mmol) of [1,3-bis(2,6-diisopropylphenyl)imidazolium]copper(I) chloride. To the flask were attached a thermometer, a Dimroth condenser, a mechanical stirrer, and a ball filter. The flask was placed in a heated silicone oil bath and the content was stirred, while air was introduced at a rate of 130 mL/min. through the ball filter, and a cooling water was passed through the condenser. At 80° C. (temperature of the reaction mixture), a yellow liquid mixture of 1.79 g (9.22 mmol) of dimethyl phthalate and 53.4 mg (0.133 mmol) of tris(acetylacetonato)rhodium was added to the reaction mixture, and the reaction mixture was further heated to reach 240° C., and stirred for 2 hours at the temperature. Then, the same liquid mixture was further added to the reaction mixture, and the reaction mixture was further stirred for 2 hours. Then, the same liquid mixture was again added and further stirred for 4 hours. After the reaction was complete, the flask was cooled in air, and the reaction mixture was diluted with methanol and water. The diluted reaction mixture was subjected to liquid chromatography. The following analytical results were obtained:

Yield: 4.0%, TON: 62, S/A: 19/81.

What is claimed is:

1. A process for preparing 2,3,3',4'-biphenyl-tetracarboxylic acid tetraester which comprises subjecting a phthalic acid diester to oxidative-coupling reaction in the presence of molecular oxygen and a catalyst comprising a rhodium-containing compound represented by the following formula:

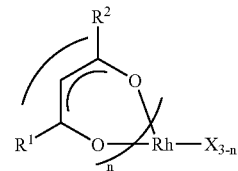

in which each $R^1$ and $R^2$ independently represents an alkyl group or an aryl group, X represents a halogen atom, and n is an integer of 1 to 3.

2. The process of claim 1, wherein the catalyst further comprises a copper-containing compound.

3. The process of claim 2, wherein the copper-containing compound is copper acetate.

4. The process of claim 2, wherein the copper-containing compound is [1,3-bis(2,6-diisopropylphenyl)-imidazolium]copper(I) chloride.

5. The process of claim 1, wherein the rhodium-containing compound is a rhodium acetylacetonato complex.

6. The process of claim 1, wherein the catalyst further comprises β-diketone.

7. The process of claim 6, wherein the catalyst further comprises a copper-containing compound.

8. The process of claim 1, wherein the rhodium-containing compound is a rhodium 1,5-cyclooctadiene complex.

* * * * *